United States Patent [19]

Sato

[11] Patent Number: 5,770,408
[45] Date of Patent: Jun. 23, 1998

[54] METHOD FOR THE AMPLIFICATION OF A BASE SEQUENCE

[75] Inventor: Yoshihiro Sato, Toyota, Japan

[73] Assignee: Laboratory of Molecular Biophotonics, Shizuoka, Japan

[21] Appl. No.: 677,944

[22] Filed: Jul. 10, 1996

[30] Foreign Application Priority Data

Jul. 13, 1995 [JP] Japan ..................................... 7-177768

[51] Int. Cl.$^6$ .............................. C12P 19/34; C12Q 1/68; C07H 21/04; C07H 21/00
[52] U.S. Cl. ............................ 435/91.2; 435/6; 536/24.3; 536/25.32
[58] Field of Search ............................... 536/24.3, 25.32; 435/91.2, 6

[56] References Cited

U.S. PATENT DOCUMENTS 4,914,210   4/1990   Levenson et al. ...................... 543/413

FOREIGN PATENT DOCUMENTS 320308   6/1989   European Pat. Off. .......... C12Q 1/68

OTHER PUBLICATIONS

Nilsson et al. Padlock Probes: Circularizing Oligonucleotides for Localized DNA Detection. Science, vol. 265, pp. 2085–2088, 1994.

Primary Examiner—Kenneth R. Horlick
Assistant Examiner—J. Tung
Attorney, Agent, or Firm—Leydig, Voit & Mayer, Ltd.

[57] ABSTRACT

The present invention relates to a method for the amplification of a base sequence A1A2 consisting of two successive base sequences, A1 and A2, in a single strand polynucleotide as an object to be amplified characterized in that said method comprising at least (1) hybridizing a probe B consisting of a polynucleotide comprising the base sequence B1 complementary to said base sequence A1, a polynucleotide comprising the base sequence B2 complementary to said base sequence A2 and a linkage portion linking the two polynucleotide via itself, with the base sequence A1A2 of said polynucleotide, as the object to be amplified, to form a hybrid, (2) ligating the 5'-end of the base sequence B1 in said probe B to the 3'-end of the base sequence B2 in the same with the aid of ligase, (3) heat denaturating the double strand formed said hybridization, (4) hybridizing said heat denaturated polynucleotide complex with another probe B or a probe A consisting of a polynucleotide comprising said base sequence A1, a polynucleotide comprising said base sequence A2 and a linkage portion linking the two polynucleotide via itself, and (5) ligating 5'-end of the base sequence B1 in said probe B to the 3'-end of the base sequence B2 in the same, or 3'-end of the base sequence A1 in said probe A to the 5'-end of the base sequence A2 in the same with the aid of ligase.

8 Claims, 2 Drawing Sheets

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 90 base pairs
        ( B ) TYPE: nucleic acid
        ( C ) STRANDEDNESS: single
        ( D ) TOPOLOGY: linear ( i i ) MOLECULE TYPE: synthetic DNA (oligonucleotide)

( x i ) SEQUENCE DESCRIPTION: SEQ ID NO:1:

```
TGCCTGCAGG  TCGACTCTAG  TTTTTTTTT  TTTTTTTTT  TTTTTTTTT  TTTTTTTTT        60
TTTTTTTTT  CGGCCAGTGC  CAAGCTTGCA                                         90
```

( 2 ) INFORMATION FOR SEQ ID NO:2:

( i ) SEQUENCE CHARACTERISTICS:
        ( A ) LENGTH: 90 base pairs
        ( B ) TYPE: nucleic acid
        ( C ) STRANDEDNESS: single
        ( D ) TOPOLOGY: linear ( i i ) MOLECULE TYPE: synthetic DNA (oligonucleotide)

( x i ) SEQUENCE DESCRIPTION: SEQ ID NO:2:

```
TGCAAGCTTG  GCACTGGCCG  TTTTTTTTT  TTTTTTTTT  TTTTTTTTT  TTTTTTTTT        60
TTTTTTTTT  CTAGAGTCGA  CCTGCAGGCA                                         90
```

( 2 ) INFORMATION FOR SEQ ID NO:3:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: synthetic DNA (oligonucleotide)

( x i ) SEQUENCE DESCRIPTION: SEQ ID NO:3:

```
TTTTCTAGA  GTCGACCTGC  AGGCATGCAA  GCTTGGCACT  GGCCGTTTTT                 50
```

METHOD FOR THE AMPLIFICATION OF A BASE SEQUENCE

BACKGROUND OF THE INVENTION

1. Field of the Invention

This invention relates to a method for the amplification of a base sequence with high sensitivity and high specificity, wherein the method uses a probe for ligase chain reaction (LCR) and enables the identification of a single base difference accurately and the facilitation of the separation of unreacted probes, and to a method for the detection of a base sequence by means of said amplification method.

2. Related Background Art

Generally, in a blotted membrane, a fixed cell and the like, a method for detecting the location of an object to be detected (for example, base sequences such as a polynucleotide or oligonucleotide) requires that the method has (1) high sensitivity which enables the detection of a trace of the object to be detected, (2) high specificity to the object to be detected for reducing background as much as possible, (3) high discrimination to enable the accurate identification of a single base difference and (4) high affinity for the object to be detected to facilitate the removal of excessive unreacted probes and the like.

In conventional methods using hybridization, a fixed object to be detected hybridizes with a labeled probe to form a hybrid and the location of the object to be detected is determined by means of detecting said label. Among those methods, for example southern hybridization, northern hybridization and in suit hybridization are well known.

However, in the above-mentioned hybridization methods, the amplification of the object to be detected is not carried out prior to the detecting operation, and thus the detecting sensitivity is low. Also, there is the problem that prior methods require a long period of several hours to several days to detect a trace of the object to be detected. Furthermore, the probe does not have sufficiently high specificity to the object to be detected, so that there are some problems. For example, that an accurate discrimination of a single base difference and the like are impossible, the specificity and identification for the object to be detected are low and the background is high. Furthermore, the separation of unreacted probes from the others has a lot of elements of trial and error, and it is also difficult to use rigorous or complete washing conditions.

SUMMARY OF THE INVENTION

For solving the above-mentioned problems accompanied with prior arts, the method has been considered which contains an amplification step before detecting an object to be detected. For example, suit polymerase chain reaction was developed by combining in situ hybridization with polymerase chain reaction (PCR). This method is superior in the point that it has high sensitivity because of the accompanying amplification. However, the disadvantage is that the background is increased due to its low specificity. Furthermore, the method does not solve the problem of an accurate discrimination of a single base difference. Furthermore, there is the problem that an operation for removing unreacted probes, for example a washing operation is limited because of amplified products not being fixed to the object to be detected, and thus the detection of the amplified products is difficult.

On the other hand, ligase chain reaction (LCR) is known as an amplification method which is based on a principle different from that of the above-mentioned PCR method, and has excellent properties (EP-A-320,308, Barany, Proc. Natl. Acad. Sci., 88, 189 (1991)). LCR, compared with PCR, has the advantage that it generally has a high specificity to an object to be detected and thus it enable the detection of the object with low background. Furthermore LCR is known as having a relatively high ability for identifying a single base difference accurately. However, in the case of detecting the location of an object to be detected by means of LCR method, separating unreacted probes from reacted probes is difficult because the reacted probes are not fixed to the object. Also, detecting the object with one step is difficult because of the necessary extraction and separation operations, such as gel electrophoresis to detect the amplified product. These problems make the LCR method insufficient to detect the location of an object to be detected.

On the other hand, the method is known in which a probe for forming the hybrid is tightly fixed to the base sequence of an object to be detected on the occasion of hybridization (Landegren et. al, Science, 265, 2085 (1994)). Accordingly, in this method unreacted probes are easily separated by the washing operation and that an object to be detected is detected. Also a reaction on the occasion of fixation is occurred only in the case of the accurate hybrid formation of both end parts of a probe, so that the method seems to have high specificity and accurate discrimination of a single base difference. However, this method leaves the problem that its detecting sensitivity is low because it is not accompanied by an operation for the amplification reaction prior to detecting an object to be detected.

Accordingly, in a blotted membrane, a fixed cell and the like, there in no method for detecting the location of an object to be detected (for example, base sequences such as a polynucleotide or oligonucleotide) which has a (1) high sensitivity which enables the detection of a trace of the object to be detected, (2) high specificity to the object to be detected for reducing background as much as possible, (3) high discrimination to enable the accurate identification of a single base difference and (4) high affinity for the object to be detected to facilitate the removal of excessive unreacted probes and the like. Thus, the development of such method is strongly desired.

The inventors of the present invention, as a result of devoted research to establish the above-mentioned goals, have found out that by preparing a probe with noble structure and by amplifying by means of LCR method as an operation prior to detecting an object to be detected, the detection method has a (1)high sensitivity which enables the detection of a trace of the object to be detected, (2) high specificity to the object to be detected for reducing background as much as possible, (3) high discrimination to enable the accurate identification of a single base difference and (4) high affinity for the object to be detected to facilitate the removal of excessive unreacted probes and the like, and thus have completed the present invention.

The present invention will become more fully understood from the detailed description given hereinbelow and the accompanying drawings which are given by way of illustration only, and thus are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DESCRIPTION OF THE PREFERRED EMBODIMENT

Figure 1:
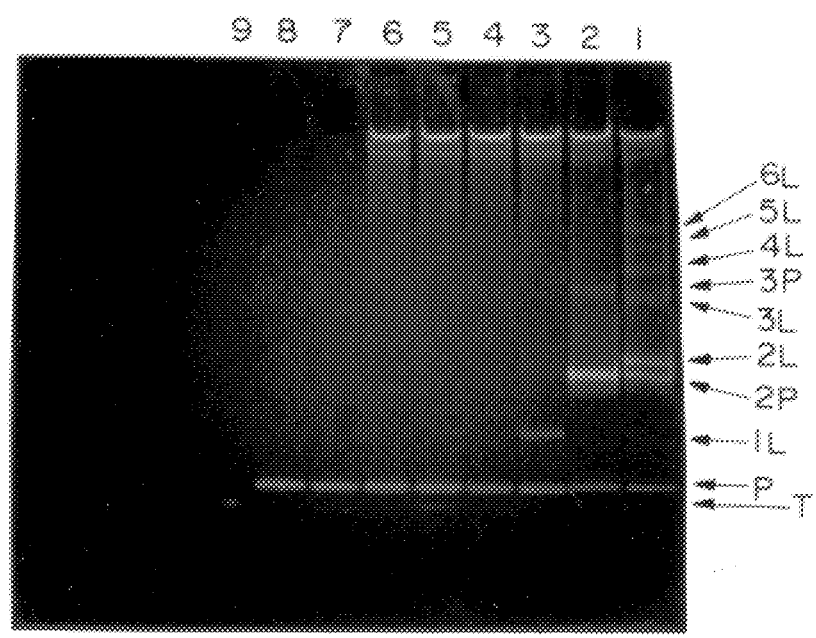
FIG. 1 shows the electrophoresis running pattern of the products of the Example. T represents the target, P represents the probe X or Y, 2 P represents the hybrid which is formed from one probe X and one probe Y, 3 P represents the hybrid which formed from a total of three of probe X and Y, 1 L-6 L represents the one in which probe A and B are circularized by means of ligase and concatenated, and the numerals 1–6 represent the number of probes.

The present invention will be explained in more detail in reference to some embodiments of the invention. In other words, the present invention relates to a method for the amplification of a base sequence, wherein use is made of two kinds of probes for the LCR amplification reaction and the base sequence is amplified by the LCR method while the amplification product is fixed to an object to be detected, and thus unreacted probes can be removed completely by means of washing and the like after the amplification operation.

Concretely, the present invention relates to a method for the amplification of a base sequence wherein among four kinds of probes which are necessary for the usual LCR method, the probe which consists of two adjacent probes on the base sequence chain to be linked by a ligase reaction and a suitable linkage portion linking the two probes via the linkage portion itself, and the probe which consists of two adjacent probes on the complementary chain to the base sequence to be linked by a ligase reaction and a suitable linkage portion linking the two probes via the linkage portion itself, are prepared, the LCR method is effected, and the probe specific to the base sequence to be detected is circularized and concatenated.

Furthermore the present invention relates to a method for the detection of a base sequence by labeling the probes and measuring the presence or variation of the base sequence to be detected in the above-mentioned base sequence amplification method according to the present invention.

More particularly, the present invention relates to a method for the amplification of a base sequence A1A2 consisting of two successive base sequences, A1 and A2, in a single strand polynucleotide as an object to be amplified. The method comprises at least (1) hybridizing a probe B consisting of a polynucleotide comprising the base sequence B1 complementary to said base sequence A1, a polynucleotide comprising the base sequence B2 complementary to said base sequence A2 and a linkage portion linking the two polynucleotides via itself, with the base sequence A1A2 of the polynucleotide, as the object to be amplified, (2) ligating the 5'-end of the base sequence B1 in said probe B to the 3'-end of the base sequence B2 in the same with the aid of ligase, (3) heat denaturating the double stranded form of said hybridization, (4) hybridizing said heat denaturated polynucleotide complex with another probe B or a probe A consisting of a polynucleotide comprising said base sequence A1, a polynucleotide comprising said base sequence A2 and a linkage portion linking the two polynucleotides via itself, and (5) ligating the 5'-end of the base sequence B1 in said another probe B to the 3'-end of the base sequence B2 in the same, or ligating the 3'-end of the base sequence A1 in said probe A to the 5'-end of the base sequence A2 in the same with the aid of ligase.

Also the present invention relates to the method for the amplification of the base sequence further characterized in that the steps (3) to (5) are repeated.

Also, the present invention relates to the method for the amplification of the base sequence characterized in that said linkage portion comprises at least a polynucleotide or hexaethyleneglycol.

Also the present invention relates to the method for the amplification of the base sequence characterized in that the length of said linkage portion is at least 1.2 to 3 times as long as that of the base sequence A1A2.

Also the present invention relates to the method for the amplification of the base sequence characterized in that in said probe A a linkage portion is linked to the 5'-end of the base sequence A1 and linked to the 3'-end of the base sequence A2 via its linkage portion, or in said probe B a linkage portion is linked to the 3'-end of the base sequence B1 and linked to the 5'-end of the base sequence B2 via said linkage portion.

Also the present invention relates to the method for the amplification of the base sequence characterized in that in said polynucleotide complex said single strand polynucleotide to be amplified is concatenated with said probe B via the cyclic structure of said probe B formed by said ligation.

Furthermore, the present invention relates to the method for the amplification of the base sequence characterized in that in said amplified product said single strand polynucleotide to be amplified is concatenated with said probe A via the cyclic structure of said probe A and the cyclic structure of said probe B formed by said ligation.

Furthermore, the present invention relates to the method for the detection of a base sequence characterized in that said method detects the amplified product produced by the base sequence amplification method.

Also, the present invention relates to the method for the detection of the base sequence characterized in that use is made of said probe A labeled or said probe B labeled by using a labeling agent.

Also, the present invention relates to the method for the detection of the base sequence characterized in that said labeling agent is selected from the group consisting of a radioisotope, a fluorescence, a digoxigenin and biotin.

Polynucleotide as an object to be detected

The Polynucleotide used in the present invention is particularly not limited, and detection can be suitably made of polynucleotide, oligonucleotide and the like which can be used in a usual hybridization reaction and LCR reaction. Furthermore, the existent form of the polynucleotide to be detected is particularly not limited, and it may be in a solution or fixed on a blotting membrane or the like. A usual LCR reaction condition is applicable in any existent form.

Although there is not a limitation particularly about the kind or length of the base sequence to be detected in a specimen, the base sequence needs to be known. For this reason, the base sequence to be detected can be determined by means of a usual base sequence analysis, such as the dideoxy method (Sanger F. et. al., Proc. Natl. Acad. Sci. USA, 74,5463 (1977)).

Probe A and B, and linkage portion

Both of two kinds of the LCR probes, A and B, used in the present invention have base sequences for forming the hybrid at both ends, and have the structure in which the base sequences are linked by means of a suitable length of linkage portion.

The base sequence of the above-mentioned essential probe A and probe B and the structure of the linkage portion are dependent upon the base sequence to be detected in a specimen. In other words, if the base sequence to be detected is successive base sequence A1A2 consisting of A1 and A2, the number of bases of A1 or A2 is not particularly limited. Generally, the number is not limited even if it is adapted to the condition used for the LCR method. Preferably, the base number of the base sequence A1 approximately equal to that of the base sequence A2. In this case the phosphodiester bond formed with the aid of ligation after hybridization is located at approximately the center of the base sequence A1 and A2.

Furthermore, according to the present invention, in probe A, the polynucleotide of the above-mentioned base sequence A1 is linked to the polynucleotide of the base sequence A2 via the above-mentioned linkage. The preparation of each base sequence of A1 and A2 is not particularly limited, and known synthetic oligonucleotides or polynucleotide can be used. Otherwise, those sequences can be synthesized by means of a usually commercial DNA synthesizer and the like (Hirao ichiro, "new basic biochemical experiment method 7, genetic engineering", Meruzen Publishers, 1998).

Similarly, according to the present invention, the probe B consists of the polynucleotide comprising the base sequence B1 complementary to the above-mentioned base sequence A1, the polynucleotide comprising the base sequence B2 complementary to the above-mentioned base sequence A2, and the linkage portion linking those polynucleotides via itself. The B1 and B2 base sequences can be synthesized using a method similar to that for the probe A.

Furthermore, in the present invention the base sequence A1 is linked to the base sequence A2 via a linkage portion to form a single strand probe A. Similarly, the base sequence B1 is linked to the base sequence B2 via a linkage portion to form a single strand probe B. The position of the linkage portion and kind and length of the linkage group used in the probe A or B are not particularly limited. The linkage should not inhibit the hybridization between the probe A or B and the polynucleotide to be detected. The linkage should also be stable under the usual LCR conditions.

Accordingly, in the present invention the linkage position is not particularly limited, and depending on the type of linkage group, there may be some cases where the linkage is preferably performed at the 3' or 5' end and some cases where the linkage is preferably performed at a position several bases away from that end.

Furthermore it seems to be necessary that the linkage position is sufficiently distant from the active center of the ligase so as not to inhibit the reaction by ligase.

The above-mentioned probe B is complementary to the polynucleotide to be detected and under hybridizing conditions forms a double-stranded structure with it. The probe B becomes cyclic when the base sequences B1 and B2 are joined with the aid of ligase, so that the single chain of the polynucleotide to be detected passes through the ring of said cyclic probe.

When forming the structure, if the length of the linkage portion is too short, the above-mentioned hybridization becomes insufficient and the above-mentioned double strand formation becomes insufficient. Thus, it is difficult for the single strand of the polynucleotide to be detected to pass through the ring of said cyclic probe and to be fixed together with the probe. Accordingly, the linkage portion must be at least 1.2–3 times as long as the base sequence A1A2 to be detected. The proper length of the linkage portion can be chosen suitably in response to the kind of linkage group and the length of the base sequence to be detected and the like.

The linkage portion and the linkage group used in the present invention are not particularly limited, and any kind, length and structure of linkage group may be used.

If an oligonucleotide is used as a linkage portion, and the oligonucleotide does not prevent the hybrid formation between the probe and the polynucleotide to be detected, the linkage portion can be synthesized with the probe simultaneously. For example, in one preferable embodiment of the present invention use is made of poly-T as the above-mentioned linkage portion.

Generally, the linkage portion of a polynucleotide should not be complementary to base sequences in the specimen in order to reduce background. Furthermore, preferably the linkage portion should not prevent ligation, and should not be complementary to the base sequence to be detected. Furthermore, in order to preserve its length, linkage portions should not have any sequence where a special structure, such as a hammer head, is likely to form.

Furthermore, preferable use is made of a polyether alcohol such as hexaethyleneglycol as a linkage portion (A. Jaechke, et al. Tetrahedron Lett. 34,301,1993). A connection between said linkage group and the above-mentioned probe base sequence is not limited, and for example when using a DNA synthesizer, the hexaethyleneglycol portion can be prepared simultaneously (for example, Clontech Inc., Spacer Phosphoramidite, Zhang, Y et al, Nucleic Acids Res., 19,3929,1991). Using hexaethyleneglycol as a linkage group enables the preparation of a long chain with a small number of synthesizing steps, thus maximizing the yield of the synthesis.

LCR reaction

The LCR condition which can be used in the present invention is not limited, and is performed according to a standard procedure (EP-A-320,308, Barany F. Proc. Natl. Acad. Sci. USA, 88, 189 (1991)). For example, ligases which are heat-resistant and can bind only to two successive DNAs hybridized on the complementary chain, are preferably used. Also, the reaction solution composition is chosen as appropriate for the above-mentioned ligase.

Also, commercially available LCR reaction kits (for example LCR kit ex STRATAGENE Inc.) can be used. The setting of the Thermal cycle is not limited, and a usual condition can be used suitably. The number of cycles is not limited, and can be set depending on the initial concentration of the object to be detected, the detection method for amplified products, the occurrence of non-specific amplification and the like.

The present invention contains furthermore that the probe A hybridizes with the above-mentioned cyclic probe B or the probe B hybridizes with the object to be detected, and that the probe A or B is circularized by ligation. For this purpose, the above-mentioned probe B is first circularized by ligation and then the resultant double strand is heat-denatured to be detached. A condition for the heat denaturation is not limited, and use can be made of a condition according to the condition used for usual PCR or LCR. For example, use can suitably be made of the condition of 92° C. for 1 minute. In this case, for example the probe A which hybridizes with the cyclic probe B consists of a polynucleotide comprising the base sequence A1, a polynucleotide comprising the base sequence A2 and a linkage portion linking the polynucleotide via itself. The probe A hybridizes with the circularized probe B. In this case, the base sequence A1A2 of the probe A is complementary to the base sequence B1B2 of the probe B and can hybridize with it. Furthermore, after hybridization the double stranded structure can be yielded. Circularizing the probe A by ligation according to the LCR condition leads to the complex in which the cyclic probe B and A concatenate with each other to form a chained structure, so that a polynucleotide to be detected and the probe, are fixed together. The condition to be used in this case is similar as the condition explained above.

In the present invention the above-mentioned steps can be repeated the desired number of times. The amplification reaction for the mixture of probe A and probe B by using usual LCR condition leads to the formation of a high molecular weight amplified product in which many of the cyclic probes A or B are fixed to the polynucleotide single chain to be detected and concatenated each other.

The base sequence of the probe prepared in this case is complementary to the base sequence to be detected, and thus high specificity is attained in the above-mentioned LCR reaction. Accordingly, background can be extremely low.

Furthermore, most of the amplified (cyclic) probes A or B have the structure in which they are fixed with each other by means of the chain structure and are fixed to the polynucleotide single strand to be detected.

Detection of Polynucleotide to be detected

Accordingly, after the reaction of the present invention, the polynucleotide to be detected, at which cyclic probe A and cyclic probe B are localized, is detected very easily. For example, said probe A and B can be labeled by means of various labeling methods and the polynucleotide can be easily detected because of the signal from the label localizing at the object to be detected. A labeling method which can be used in the present invention is not limited, and use is made of known labeling methods. For example, use is made of labeling with a radioactive isotope, digoxigenin or a fluorescence reagent, and the like.

Furthermore, in the present invention excess or unreacted reagents such as labeled probes can be easily removed. For example, if the present invention is practiced in solid phase, repeated washing can remove excess or unreacted reagents, labeled probes and the like . The affinity between cyclic probes fixed with each other by means of a chain structure and the object to be detected is extremely high, so that the affinity will hardly be broken by a normal washing procedure.

In the present invention a position for labeling is not limited and can be any part of a probe as long as it does not prevent ligation.

Although the present invention seems to be particularly useful for the detection of a target nucleic acid which is fixed on a solid phase, it can also be use for labeling, modifying, detecting and the like for a target nucleic acid in liquid phase. In this case, since a new product with a high molecular weight is yielded after completing the reaction according to the present invention, the results can be confirmed by usual gel electrophoresis and the like.

EXAMPLE

The present invention will be explained with the reference to the following example. However it is to be understood that the present invention is not intended to be limited to the specific embodiment and variations may be made by one skilled in the art without departing from the spirit and scope of the present invention.

(1)Synthesis of probe X, probe Y and target nucleic acid

An oligonucleotide having the base sequences described in the sequence identification numbers 1, 2 and 3 are synthesized as probe X, probe Y and target, respectively, and use is made of those. Probe X and Y are synthesized by means of the DNA synthesizer Model 394 (Perkin Elmer Inc.), and the target is synthesized by means of the DNA synthesizer Expedite 8909 (Perseptive BioSystems Inc.). The resultant oligonucleotides are isolated and purified by means of reverse phase high performance liquid chromatography (HPLC).

The purification condition are as follows:

| oligonucleotides | probe X, Y | target |
|---|---|---|
| HPLC system | Shimazu Seisakusyo | LC-6A Waters 800 |
| HPLC column | capsule pack C18 | delta pack C18 |
| elution solvent | acetonitrile 15 - 40%/0.05 M TEAA | |
| buffer solution | | |
| flow rate | 1.0 ml/minute | |
| detection wave length | 254 nm | |

The prepared oligonucleotides are recognized as single peaks.

(2)Phosphorylation of the 5'-ends of probe X and probe Y

The 5'-ends of probe X and probe Y obtained above are phosphorylated by the following method, respectively. In other words, 50 $\mu$l of the solution, containing the above-mentioned probe (50 pmol), ATP (1.5 nmol), T4 polynucleotide kinase (20 U, Takara copr.), $MgCl_2$ (10 mM), dithiothreitol(DTT) (50 mM), glycerol (5%) and Tris-HCl (50 mM, pH 9.5), is reacted at 37° C. for 30 minutes. After which 20 U of T4 polynucleotide kinase is added to the solution and reacted at 37° C. for 30 minutes.

(3) LCR reaction

By using the LCR kit of STRATAGENE Inc., LCR is performed according to the following conditions. The reaction solution is 20 $\mu$l and its composition consists of Tris-HCl (20 mM, pH 7.5), KCl (20 mM), $MgCl_2$ (10 mM), NP-40 (surface active agent, STRATAGENE Inc., 0.1%), ATP (0.1 mM), dithiothreitol (1 mM), salmon sperm DNA (500 ng) and PfuDNA ligase (4 U). To this solution the above-mentioned probe X or Y (5 pmol) or the target (0.5 pmol) was added according to the following table.

| sample No. | 1 | 2 | 3 | 4 | 5 | 6 |
|---|---|---|---|---|---|---|
| probe X | + | + | + | + | − | − |
| probe Y | + | + | − | − | + | + |
| target | + | − | + | − | + | − |

+: present
−: absent

By means of the Thermal cycler (Perkin Elmer Inc.), (GeneAmp PCR System 9600), the reaction is first performed at 92° C. for 1 minute and then at 60° C. for 3 minutes. Following that, the reaction cycle of 92° C. for 1 minute and 60° C. for 1 minute is repeated 25 times.

(4) The above-mentioned reaction mixture was separated by polyacrylamide gel electrophoresis (use being made of polyacrylamide homogeneous gel, 7.5 % concentration), after which each product was measured.

Referring to FIG. 1, electrophoresis running patterns are shown of the above-mentioned reaction mixture (lanes 1–6), probe X (5 pmol, lane 7), probe Y (5 pmol, lane 8) and the target (1 pmol, lane 9).

As shown in FIG. 1, the band P is seen on the lanes 1–8 and is derived from probe X or Y, and the band T in lane 9 is derived from the target.

As shown in the figure, only lane 1 shows that many bands with high molecular weight are produced. To produce such bands, it is necessary for the above-mentioned probe X, Y and target to exist together. Accordingly, this results shows that the probe X and Y and the target exist together and are fixed together.

Figure 2:
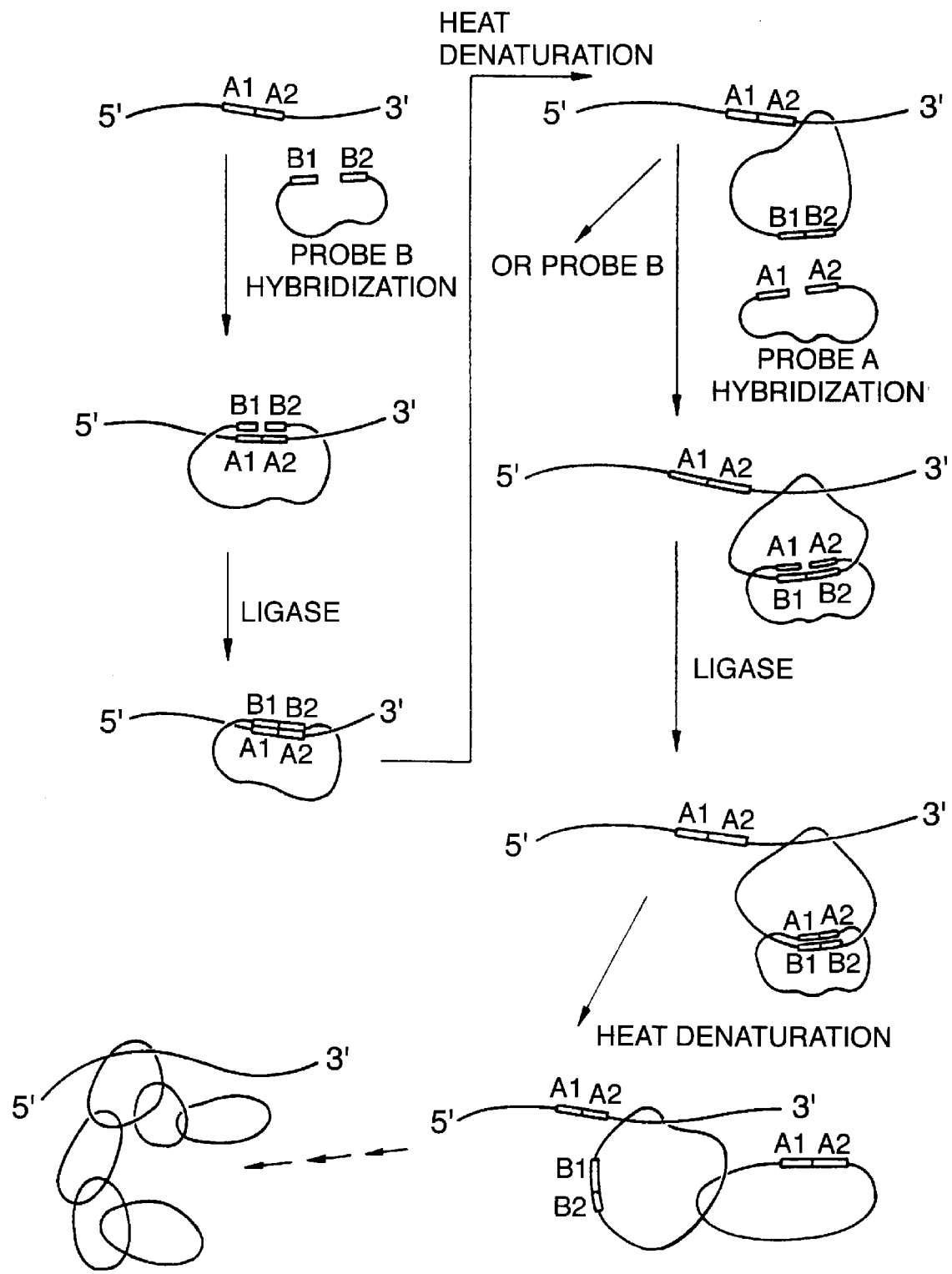
FIG. 2 shows outlines of the principle of the present invention.

Also, the distribution of molecular weight as seen in FIG. 2 clearly shows that in this example according to the present invention the existence of the amplified product comprising at least six probes is recognized.

The gene amplification detection method according to the present invention is characterized by its high sensitivity, high specificity and ability for detecting a single base difference to the same extent as LCR. Further, the amplified product is tightly fixed to the target nucleic acid. Accordingly, the present invention is an improvement over the prior art for the detection of target nucleic acid fixed on solid phase. Also the present invention is useful as a novel labeling, modifying and detecting method for the target nucleic acid in liquid phase.

From the invention thus described, it is obvious that the invention may be varied in many ways. Such variations are not to be regarded as a departure from the spirit and scope of the invention, and all such modifications as would be obvious to one skilled in the art are intended to be included within the scope of the following claims.

The basic Japanese Application No.177768/1995 filed on Jul. 13, 1995 is hereby incorporated by reference.

What is claimed is:

1. A method for the amplification of a target base sequence A1A2 consisting of two successive base sequences, A1 and A2, in a single strand polynucleotide, which method comprises:

(1) forming a first complex comprising said single strand polynucleotide interlocked with a ligated first probe B looped around said single strand polynucleotide by:

(i) hybridizing, with the target base sequence A1A2 of the single strand polynucleotide, the probe B consisting of a polynucleotide comprising the base sequence B1 complementary to said base sequence A1, a polynucleotide comprising a base sequence B2 complementary to said base sequence A2, and a linkage portion linking the two B1 and B2 polynucleotides, (ii) ligating the 5'-end of the base sequence B1 in said probe B to the 3'-end of the base sequence B2 in said probe B, and
(iii) heat denaturing;
(2) forming a second complex comprising said first complex and a first probe A interlocked with said first probe B in said first complex by:
(i) hybridizing, with the base sequence B1B2 of said looped first probe B, the probe A consisting of a polynucleotide comprising the base sequence A1 complementary to said base sequence B1, a polynucleotide comprising the base sequence A2 complementary to said base sequence B2, and a linkage portion linking the two A1 and A2 polynucleotides,
(ii) ligating the 5'-end of the base sequence A1 in said probe A to the 3'-end of the base sequence A2 in said probe A, and
(iii) heat denaturating,
(3) interlocking another probe A with the base sequence B1B2 of said looped probe B in said second complex by steps (2)(i)–(iii), or interlocking another probe B with the base sequence A1A2 of said looped probe A in said second complex by steps (1)(i)–(iii) with the proviso that the base sequence A1A2 is of said looped probe A, and
(4) repeating step (3) to form a structure with concatenate strands, thus amplifying the base sequence A1A2 of the single strand polynucleotide by amplifying the number of looped probes A and B fixed to said single strand polynucleotide.

2. The method for the amplification of the base sequence according to claim 1 wherein said linkage portion comprises at least a polynucleotide or hexaethyleneglycol.

3. The method for the amplification of the base sequence according to claim 2 wherein the length of said linkage portion is at least 1.2 to 3 times as long as that of the base sequence A1A2.

4. The method for the amplification of the base sequence according to claim 2 wherein in said probe A a linkage portion is linked to the 5'-end of the base sequence A1 and linked to the 3'-end of the base sequence A2 via itself, or in said probe B a linkage portion is linked to the 3'-end of the base sequence B1 and linked to the 5'-end of the base sequence B2 via itself.

5. The method for the amplification of the base sequence according to claim 1 wherein in said amplified product said single strand polynucleotide to be amplified is concatenated with said probe A via the cyclic structure of said probe A by said ligation and the cyclic structure of said probe B formed by said ligation.

6. A method for the detection of a base sequence wherein said method comprises carrying out the method according to claim 1 to produce an amplified product and detecting the amplified product.

7. The method for the detection of the base sequence according to claim 6 wherein said probe A is labeled with a labeling agent or said probe B is labeled with a labeling agent.

8. The method for the detection of the base sequence according to claim 6 wherein said labeling agent is selected from the group consisting of radioisotope, fluorescence, digoxigenin and biotin.

* * * * *